United States Patent
Ryan et al.

(10) Patent No.: US 10,978,197 B2
(45) Date of Patent: Apr. 13, 2021

(54) HEALTHCARE WORKFLOWS THAT BRIDGE HEALTHCARE VENUES

(71) Applicant: CERNER INNOVATION, INC., Kansas City, KS (US)

(72) Inventors: Hugh H. Ryan, Lee's Summit, MO (US); Frank Azzaro, Olathe, KS (US)

(73) Assignee: CERNER INNOVATION, INC., Kansas City, KS (US)

(*) Notice: Subject to any disclaimer, the term of this patent is extended or adjusted under 35 U.S.C. 154(b) by 771 days.

(21) Appl. No.: 15/381,390

(22) Filed: Dec. 16, 2016

(65) Prior Publication Data
US 2017/0177805 A1      Jun. 22, 2017

Related U.S. Application Data

(60) Provisional application No. 62/269,527, filed on Dec. 18, 2015.

(51) Int. Cl.
*G16H 40/20*      (2018.01)
*G16H 10/60*      (2018.01)

(52) U.S. Cl.
CPC ............. *G16H 40/20* (2018.01); *G16H 10/60* (2018.01)

(58) Field of Classification Search
CPC combination set(s) only.
See application file for complete search history.

(56) References Cited

U.S. PATENT DOCUMENTS

| | | | |
|---|---|---|---|
| 2006/0235280 A1* | 10/2006 | Vonk et al. | |
| 2010/0004948 A1* | 1/2010 | Toomey et al. | |
| 2012/0215560 A1* | 8/2012 | Ofek et al. | |
| 2013/0085781 A1* | 4/2013 | Navani et al. | |
| 2014/0324469 A1* | 10/2014 | Reiner | |
| 2015/0039343 A1* | 2/2015 | Cline et al. | |
| 2015/0294089 A1* | 10/2015 | Nichols | |
| 2016/0125142 A1* | 5/2016 | Awad | |
| 2016/0259902 A1* | 9/2016 | Feldman et al. | |
| 2017/0300634 A1* | 10/2017 | Chiang et al. | |
| 2018/0089385 A1* | 3/2018 | Gupta et al. | |

* cited by examiner

*Primary Examiner* — Michael Tomaszewski
*Assistant Examiner* — William T. Monticello
(74) *Attorney, Agent, or Firm* — Shook, Hardy & Bacon L.L.P.

(57) ABSTRACT

A computerized system customizes patient care workflows for health service providers. The system may extract essential details from various health service records for an individual, transform those details into standardized information, and use the standardized information to generate health service workflows that are particular to the patient. The health service workflows may be customized to a particular health service venue, a particular health service provider role, or even a particular health service provider.

18 Claims, 4 Drawing Sheets

HEALTHCARE WORKFLOWS THAT BRIDGE HEALTHCARE VENUES

CROSS-REFERENCE TO RELATED APPLICATION

This application claims the benefit of U.S. Provisional Patent Application No. 62/269,527, filed Dec. 18, 2015, which is hereby incorporated by reference in its entirety.

TECHNICAL FIELD

The present disclosure relates to systems, methods, and media for generating and customizing health service workflows in the context of a Health Information Technology (HIT) system.

BACKGROUND

Some Health Information Technology (HIT) and Electronic Medical Record (EMR) software provide modified workflows or informational alerts for health care providers based on data in an individual's medical record. Generally, these special workflows are based on coarse cohorts of patients, such as patients with diabetes. The workflows reflect a known condition or symptom in the patient's medical record, usually limited to information obtained in a particular healthcare venue. For example, a nurse practitioner in a clinic may see information about the patient from past visits to that clinic, but not have information about a patient's recent visit to a different clinic, or medications prescribed by a healthcare practitioner unaffiliated with the nurse practitioner's clinic.

BRIEF SUMMARY

This brief summary is meant to present an overview of concepts related to this disclosure, and is expressly not meant to define or identify key elements of the disclosure in isolation from the remainder of the disclosure, including the figures.

The present disclosure generally relates to systems, methods, and media for customizing a patient care workflow. The systems, methods, and media may involve searching for health service records for a particular patient within and/or outside of a particular HIT system. Standardized information from the health service records may be compared to situationally recommended health service workflows associated with a patient's symptoms and/or conditions and generate recommended health service workflows for the patient. The role of a user of a patient care documentation system may be identified, and the health service workflows may be segmented based on whether the user, in the user's role, can act on a particular workflow. Of the workflows actionable by the user, workflows may further be eliminated if they are duplicative, or if it appears from the standardized information that the workflow is already in process, or if it appears from the standardized information that the workflow is complete and up-to-date, or if the workflow is untimely.

The health service records may be retrieved from two or more different health service venues, which may be healthcare venues, health-related venues, or a combination thereof. The health service records may be related to the same or similar conditions or symptoms, or to different conditions or symptoms. Information may be extracted from the health service records. If the information is not extracted in standardized form, the information may be transformed to standardized information. The health service records may comprise one or more of insurance claim records, clinical records, wellness records, satisfaction records, payer records, and pharmacy records. The standardized information may be compared to a medical knowledge model to infer possible conditions or symptoms for the patient.

The health service workflows may comprise one or more of recommended orders for the user to place, recommended tasks for the user to complete, recommended condition review, recommended assessment, educational or reference material for the user or the patient, or a combination thereof. Recommended health flows which are not actionable by a user may be transferred to one or more additional users for whom the recommended health service workflows would be actionable. If health service workflows are transferred to another user, those health service workflows may be culled of duplicative workflows, workflows which appear to be in-process, workflows which appear to be complete and up-to-date, and workflows which are untimely. The health service workflows may be customized for the user based on the venue in which the user is addressing the patient and/or based on user-indicated preferences.

Additional objects, advantages, and novel features of the disclosure will be set forth in part in the description which follows, and in part will become apparent to those skilled in the art upon examination of the following, or may be learned by practice of the disclosure.

BRIEF DESCRIPTION OF THE SEVERAL VIEWS OF THE DRAWING

The disclosure references the attached drawing figures, wherein.

DETAILED DESCRIPTION

As used herein, "health" may refer to traditional, Western-style "healthcare," which includes preventative exams and testing, prophylactic treatments and/or medications, therapeutic treatments and/or medications, palliative treatments and/or medications, and the like. As used herein, "health" may also refer to wellness-related activities or decisions, including dietary choices, dietary supplementation, day-to-day physical activity (as distinguished from physical activity undertaken with the supervision of a licensed health care provider, such as a physical therapist), and the like.

As used herein, "healthcare providers" are providers, typically licensed, who provide clinical services, such as physicians, radiologists, pathologists, audiologists, nutritionists, dieticians, psychologists, psychiatrists, mental health counselors, nurses, nurse practitioners, physician assistants, medical assistants, chiropractors, massage therapists, acupuncturists, and the like. "Health-related providers" are providers who may or may not be licensed, such as personal (physical) trainers, exercise instructors or coaches, some health coaches (a registered nurse or other licensed professional might also serve as a health coach), chefs, home health assistants, and others who may provide health-related information, encouragement, modeling, tracking, and the like, but do not provide medical or clinical services per se.

As used herein, "health service providers" include healthcare providers and health-related providers.

As used herein, "health intervention" includes medical advice and medically advised activities, treatments, medications, and the like, intended to ameliorate or cure an existing health condition. Unless specified as a "medical health intervention", "health intervention" also includes "wellness interventions", which include advice and activities intended to maintain or promote wellness, such as coaching or encouragement to make healthy lifestyle choices related to diet, physical activity, and the like. Health interventions include some activities which might be medical health interventions and/or wellness interventions, such as measurements of body mass index.

As used herein, "Health Information Technology system" or "HIT system" is used to describe a broad variety of computerized software for managing and tracking health care. An HIT system may encompass an Electronic Medical Record (EMR) system for creating, storing, modifying, deleting, viewing, and transferring healthcare records associated with a patient. In the broader context of health-related services, a "patient care documentation system" may or may not be software specifically designed for health records. For example, a personal chef or personal trainer may keep notes about a client's appointments, preferences, progress, or requests in software designed for keeping lists, word processing, calendaring, contact management or the like. As used herein, a "patient care documentation system" embraces any computerized system used by a health services provider to document information about a patient and/or an encounter with a patient. Of course, non-clinical health service providers may also have access to and use a more formal HIT system, of their own, in connection with a broader healthcare delivery organization, or as part of a Health Information Exchange (HIE). An HIE is software or a service that aims to connect distinct HIT systems for the purpose of sharing information between health service providers and interested individuals who do not use a shared patient care documentation system.

All steps and flowcharts described herein, including in the attached figures, are meant to be illustrative. It should be understood that other steps may be used with the illustrated steps, and, further, that some steps may be useful without the practice of other steps included in the figures. The illustrated sequence of steps is also exemplary, and, unless described otherwise, the steps may be performed in different sequences, combinations, and/or subcombinations.

One of the frustrations of working with HIT systems is that it is often easier to get data into the system than to retrieve data, particularly if a user is uncertain whether particular data exists or does not know how the data is stored or described within the HIT system. Data recorded in a different HIT system or outside of any HIT system may be inaccessible to the user of a particular HIT system, or may require accessing multiple systems to obtain complete information. Still further, even when records external to a particular HIT system are available, such as records accessible only through an HIE or alternate communication outside the originating HIT, they may use different file formats, different data formats, and/or different ontologies, requiring the user to manually "translate" information from different sources before it can be used, particularly, but not exclusively, before it can be used for comparative purposes. The modified workflows available in conventional HIT and EMR software are only a modest improvement over charts that present patient history uniformly from patient-to-patient. Most of the coarse filters used to modify healthcare workflows are too broadly defined to make significant reductions in the amount of effort required by a healthcare provider to efficiently locate all relevant information and draw a conclusion about next steps. For example, if a "smart" chart recognizes that a patient is being treated for diabetes, and provides modified views or workflows for diabetic patients, generally, those views or workflows may exclude information the health care provider would like to see for a particular patient, and may include tasks or information that are not relevant for a particular patient. Modifications in conventional HIT or EMR systems rarely reflect information from outside a particular organization (such as a hospital, clinic, or private medical practice). As a result, the modified workflows do not typically reflect interrelated services or orders for the patient, or other information about the patient, that may arise in different venues (e.g., a medical practice, a clinic, a hospital, a physical therapy practice, a chiropractor's office, a pharmacy, a payer database, etc.). Further, the modified workflows may be addressed to specific providers, and do not typically address health-related services that are not routinely included in Electronic Medical Records (EMRs). Still further, the modified workflows are typically retrospective. For example, a surgeon may be able to see detailed information about a patient's in-patient care at a particular hospital, and may have access to at least partial records related to the patient's pre-surgical diagnosis and preparatory care, but have no visibility into the patient's post-surgical care plan.

In some aspects, this disclosure relates to a method for customizing a patient care workflow. Two or more health service records for a patient may be identified. The health service records may reside within the same patient care documentation system, or in two or more distinct systems. If the health service records reside in different patient care documentation systems, those patient care documentation systems may reside under the umbrella of a particular HIT, or in separate HITs under the umbrella of an HIE, or in entirely separate systems. Similarly, the records may reside on the same or different servers.

The information in the health service records may be in a standardized format. For example, the health service records may be maintained using the same software, such as the same EMR software, such that the information in one record is recorded using the same storage format and the same database ontology as in the second record. If the information is not in the same format or ontology, even minor differences can significantly complicate the process of matching like tests, observations, information, etc. for a computer, which does not inherently apply intuition and contextual analysis as a human would. For example, if one health service provider records an observation of a patient's left foot, and another notes charcot arthropathy, a generic computer search function will not recognize that the observations are likely related. Where records have different formats, codes, or ontologies, an ontology mapper may be used to link related concepts from different records. An exemplary ontology mapper is described in U.S. Pat. No. 8,856,156, which is herein incorporated by reference in its entirety.

The health service role of a user of a patient encounter documentation system may be identified. The health service role of a user may be specified as part of the process for enrolling the user or granting the user access to the system. The health service role of a user may be indicated by the user, possibly on a case-by-case basis. For example, a nurse in a community clinic may sometimes attend patients as a clinical care provider, and sometimes attend patients in the capacity of a health coach or surveyor of satisfaction with a particular health service or health intervention. Exemplary roles include a treating physician, a consulting physician, a primary care physician, a nurse, a radiologist, a pathologist, an emergency department physician, an oncologist, a dietician, a pharmacist, a surgeon, a home care nurse, and the like. Roles may be defined by the organization hosting the patient encounter documentation system, and may be defined to reflect how different health service providers typically interact within or between organizations, and/or the venue in which the health service provider works.

Based on information gleaned from the patient's medical records, a database of health service workflows may be consulted to identify recommended health service workflows associated with a patient's symptoms and/or conditions and generate recommended health service workflows for the patient. The database of health service workflows may be included in a medical knowledge model or may be a standalone database. The initial group of recommended health service workflows could be extensive, addressing a variety of conditions and symptoms and presenting information, tasks, and orders that are not typically completed by any one health service provider, or even at any one health service venue. For example, the presentation of three patient symptoms could reasonably generate 30 to 50, or even more, recommended workflows. Without further processing, three-quarters or more of the recommended workflows may be irrelevant to the current user. A relatively high percentage of recommended workflows that are not actionable by or relevant to the current user may make it difficult for the user to ensure that his or her tasks have been completed before closing the record. For example, a medical technician in a clinic who is confronted with 15 or more workflows, of which only 5 are relevant to the medical technician, is much more likely to overlook a task if presented with all 15 workflows than if presented with only the 5 workflows the medical technician is responsible for completing.

Figure 1:
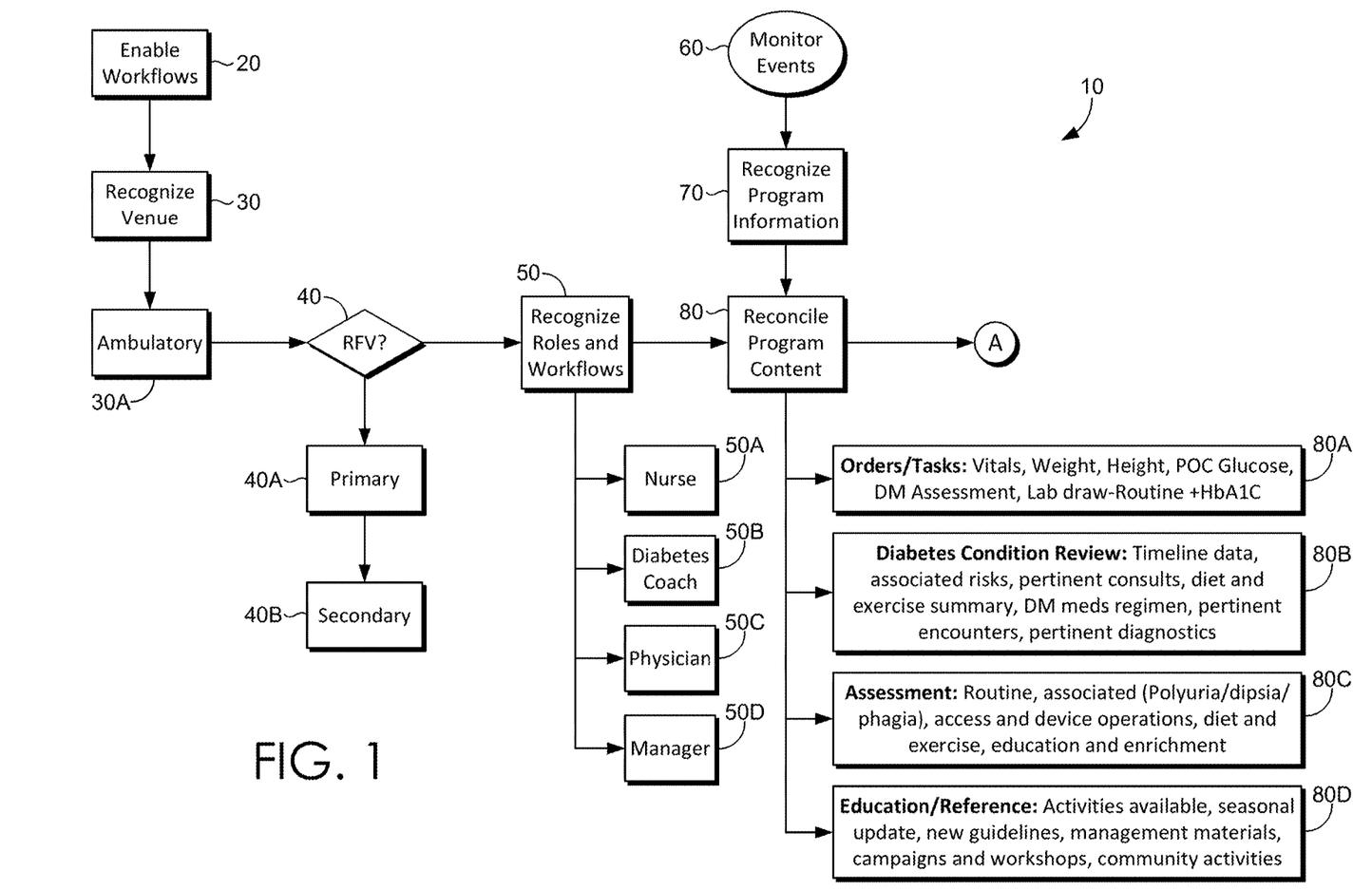
FIG. 1 is a flowchart of an exemplary process for determining context for a patient health service workflow.

An exemplary process 10 for identifying context for a patient care workflow is shown in FIG. 1. The process may be carried out on a computerized system, networked as necessary or appropriate to access all required computing and/or information resources. A workflow initiation 20 may be triggered by opening an EMR or patient encounter documentation system file for a particular patient. The workflow initiation may be automatic, e.g., if the user requests a file, the system may automatically initiate a workflow. The workflow initiation may be user-initiated, e.g., the user may request workflow initiation, as opposed to merely viewing data from the patient file.

On initiating a workflow, a venue type 30 for the workflow is determined. The workflow software may be installed on a local machine and programmed to know its venue, e.g., neighborhood clinic. Alternately, if the workflow software is being served from a geographically remote building or location, or otherwise serves multiple venue types, the workflow software may have a log-in procedure that identifies the user. Venue may be recognized as part of a user profile established when the user enrolls or is granted access to the workflow software, or the user may be asked during log-in to identify or confirm the venue. Alternately, or in addition, a user role may be defined in a way which indicates a venue, possibly even a department or unit within a venue, e.g., registered nurse—hospital—ICU.

FIG. 1 shows the venue as an ambulatory care facility 30A, however, a similar process would follow for other possible venues, including, without limitation, acute care settings, self-care settings, extended care settings, home care settings, and retail pharmacies. Having identified the venue, initial encounter content is analyzed at step 40 to determine the reason for visit (RFV). The initial encounter content may come from information provided by the patient when making an appointment, when checking in at the venue, and/or during an initial interview at the start of the encounter. A visit often has more than one motivating reason, and so a primary RFV 40A may be identified to prioritize workflows. For example, a patient with previously diagnosed Chronic Obstructive Pulmonary Disease (COPD) may complain of a cough. However, a persistent cough is a common symptom of COPD. A health service provider may recognize this and designate the COPD condition as the primary reason for the visit, identifying cough as a secondary RFV 40B. Alternately, the computing system may consult a medical knowledge model or medical database, identify the cough as likely related to the COPD, and prioritize the condition over the symptom, reaching the same result as the astute health service provider. If the computing system determines an RFV and/or prioritizes two or more RFVs, a health service provider may be asked to confirm the RFV and/or the prioritization of two or more RFVs. This enables a health service provider to override the system inferences about the RFV or RFV prioritization, if needed. The computing system, in consultation with the medical knowledge model, may consider one or more of many possible factors in prioritizing RFVs, including, without limitation, the relative severity of symptoms or conditions, the relative durations of the symptoms or conditions, location, consultations, diagnostic results, symptoms, comorbidities, medications, and combinations thereof.

Once the primary RFV has been determined, the system can look for recommended health service workflows associated with that RFV. The system can then check the workflows against user information, shown as step 50 in FIG. 1. For example, in an ambulatory care center, the user may be a nurse 50A, coach 50B, physician 50C, or manager 50D. Workflows may be screened for actionability by the user. For example, a nurse, coach, or manager will not typically have the ability to order prescription narcotics. If prescription narcotics are recommended for a particular patient, that workflow would need to be redirected to a physician or other professional with authorization to issue that order.

In contrast, certain information may be needed to assess the patient's condition and/or the progress of the patient's condition over time. Patient history, patient complaints, biometrics, and other data collection may be typically completed by a nurse or medical technician. Workflows related to patient history, patient complaints, biometrics, and other data collection may be preferentially directed to a nurse or medical technician rather than a physician or office manager. The correlation between a particular workflow and a health service provider role may be learned over time. For example, the system may monitor which workflows are completed by a given user, and assign the same and/or similar workflows to others in that role in the future. As another example, the system may deduce a relationship between a workflow and a role based on user permissions. For example, if only certain roles are allowed to order certain medications or procedures, then a workflow to order those medications or procedures must necessarily go to someone with authorization to place the order. Workflows, particularly, but not exclusively, custom workflows developed for a particular medical specialty, a particular health care delivery organization, and/or a particular venue may specify which role or roles should be associated with a particular workflow. Some combination of these approaches may be used, and users may further be permitted to reassign workflows as needed. User role definitions may be broad (e.g., all hospital nurses), intermediate (e.g., all medical-surgical nurses), fine (e.g., all medical-surgical nurses having more than 5 years tenure in this role, or all second shift pharmacy technicians), or even unique to an individual (e.g., Nurse D. Smith), allowing for tailoring the assignment of workflows to individuals or groups of individuals as desired by a particular organization.

During an encounter, a system may monitor events, shown as step 60. This may involve analyzing new data as they are added to the documentation of an encounter with the patient. The system may recognize program information at step 70. For example, the system may determine the format, form and ontology of the health service records available, and extract relevant data, transforming the data to standard format, if needed. At step 80, the system may attempt to reconcile program content with the user input and the program information. That is, the system may use the evolving data being added to the patient record, taking into account the context of the venue and the user, to refine the recommended health service workflows.

Exemplary workflows may include recommendations for orders or recommendations for patient-centered tasks 80A, condition review 80B, assessment or documentation 80C, and/or the provision of educational or reference materials for the user and/or the patient 80D. Condition reviews may provide a structured review of critical data over time. For example, for a diabetic patient, a diabetes condition review may involve presenting to a user timeline data, associated risks, pertinent consults, a diet summary, an exercise summary, Diabetes Mellitus (DM) medication regimen (for patients with Type 2 diabetes), pertinent encounters, pertinent diagnostics and/or combinations thereof, in one view or in a series of linked views associated with the condition review. Condition reviews may be simplified or complex, depending on the condition, the venue, and/or the user. Simplified condition reviews may involve fewer parameters or less detail, while complex condition reviews may involve more parameters or more detail. The user may be given the option to move between simplified and complex condition reviews. An advantage of a condition review is the ability of the user to review highly relevant data without having to "hunt-and-peck" for menu options or particular entries within a longitudinal record.

Once refined, the recommended workflows or workflow modifications can be communicated to the care team at step 90, typically by populating patient encounter documentation systems with the desired workflows at step 100, so that the workflows are present at the health service provider's next encounter with the patient. The workflows may manifest as worklists 100A, a care plan (sometimes referred to as an Interdisciplinary Plan of Care or IPOC) 100B, a condition module for tracking key information about a particular diagnosis or symptom 100C, documentation of completed work 100D, and/or educational or reference materials 100E. A care plan may be particularly helpful for providing a long-range view of recommended healthcare services, such as follow-up testing or recurring treatments. Follow-up testing or treatment can be monitored and is visible to the user, but there is no workflow inserted into a task list or alert list for the health service provider for something that does not need to be done for weeks, months, or years (e.g., repeat a certain screening procedure in 5 years).

As health services are provided at step 110, the system continues to monitor events, shown as step 60, and communicate updates to the care team, shown as step 90. The care team may comprise a variety of health service providers in different venues. As an example, a patient in need of a knee replacement may have a care team comprising a primary care physician, a nurse at the physician's office, a phlebotomist at the physician's office, an orthopedist, a nurse at the orthopedist's office, an orthopedic surgeon, one or more surgical nurses, two or more medical/surgical nurses, a physical therapist, a pharmacist, a pharmacy technician, and/or other providers associated with the physician's office, the orthopedist's office, a hospital, a physical therapy practice, and possibly other venues.

If a patient is referred or transferred to a new health service provider or new health service venue, shown as step 120, the system can provide an up-to-date overview of all of the care that has been provided across a broadly defined care team, which may include a variety of venues, providers, and services. Whether or not a patient's care team or care venue changes, the system allows for seamless coordination of a potentially dispersed care team, with each member clearly understanding which tasks, education, or services he or she is responsible for. Tasks and services assigned to other members of the care team will not show up, or will not prominently show up, in a health service provider's worklist. That is, a health service provider may be able to view the services and care plan for the entire care team, and may have a separate view or worklist that separates out the workflows for which the user/health service provider is directly responsible. At the same time, all members of the care team share access to up-to-date information about the patient, including, as non-limiting examples, biometrics, laboratory test results, examination observations, recent symptoms and complaints, or a complete list of medications, possibly including self-administered medications, allergies, and/or other contraindications. If the system encompasses health-related providers, the care team may also have visibility into a patient's non-medical activities and efforts to improve or maintain his or her health, such as physical exercise, dietary modifications, support groups, and the like.

Tasks which are incomplete and uninitiated (as opposed to in-process but not yet complete) after a recommended start date may highlight gaps in care, and the system could then introduce a workflow for referring the patient to a health service provider in a different user role. For example, if an angiogram is recommended for a patient, and the recommendation is not acted upon by the primary care physician (PCP), the system may recognize that an angiogram would typically be performed by a cardiologist, and recommend a referral to a cardiologist. The cardiologist may be a cardiologist identified in the patient's health service records (e.g., a cardiologist the patient has seen before), or a new health service provider for the patient. Depending upon the scope of information sources accessible by the system, the recommended cardiologist may be selected based upon one or more of geographical proximity to the patient's home, work, or most-visited health service provider; cardiologists who accept the patient's insurance or otherwise have existing arrangements with a payer for the patient; cardiologists who have experience with patients with similar conditions, co-morbidities, or symptoms as the current patient; patient needs and/or preferences, such as a service provider of a particular gender or age, a service provider with certain language skills, a service provider familiar with a particular religious, cultural, racial, or ethnic population, and the like.

The recommended workflows may be sorted by user role, and may further be culled and/or modified to maximize efficiency. Duplicative workflows, such as might arise if two or more symptoms or conditions each correspond to the same or similar workflows, may be eliminated. Eliminated workflows are not presented to any care provider for further action. Similarly, workflows for tasks which appear to be in-process may be eliminated, or they may be modified to a confirmation or inquiry step. For example, if an order MRI workflow is generated for two or more health service providers, and one or more health service records for the patient show an MRI has been scheduled, the order MRI workflow may be eliminated, or it may be modified to alert the provider to remind the patient about the appointment and/or confirm that the patient is aware of and intends to keep the appointment.

Workflows which appear to be complete and up-to-date may be eliminated and/or modified. For example, a workflow suggesting regular foot examinations for diabetic patients may be eliminated if the patient's health service records indicate that a foot exam was performed recently. Alternately, a workflow suggesting regular foot examinations for diabetic patients may be modified to recommend checking the status of a lesion or other area of concern discovered during a recent foot exam, possibly by a different provider in the same or a different venue. Workflows may also be eliminated or held in abeyance if the workflow is untimely. For example, if a recommended workflow indicates that a patient should have an annual preventative screening, and the patient had the recommended screening 8 months ago and has an upcoming appointment with a health services provider whose user role can receive the screening workflow, the workflow may be eliminated from the immediate encounter workflow (at the 8 month date) and/or modified to alert the provider to remind the patient about the appointment and/or confirm that the patient is aware of and intends to keep the appointment. Additionally or alternatively, the workflow to perform the screening may be transferred to the health service provider who has the upcoming appointment with the patient. If the workflow is not transferred, it would be regenerated when recommended workflows are generated at the patient's upcoming appointment.

If one or more workflows are identified for transfer to another user, those workflows may be transferred as-is, or may be culled or modified for efficiency prior to transfer. If the transferred workflows are not culled or modified for efficiency at the time of transfer, they would be culled or modified for efficiency at the time the workflow is regenerated when the transferee user next sees the patient.

By capturing data from disparate sources, including non-traditional or health-related non-healthcare records, assigning workflows based on user roles, and/or providing a care plan visible to all or a greater portion of a care team, best practices are more easily adopted and followed, with fewer gaps in care. Methods, systems, and media as described herein have the potential to immediately improve patient care and health service provider efficiency within traditional venues (e.g., a hospital or a clinic), and the potential benefits grow as a system is expanded to more venues and/or to health-related providers. The logic can be extended even to community institutions like schools, grocery stores, and fitness facilities, with automated tracking and/or patient-provided data used in lieu of health service provider entries into the system in some cases. For example, purchases made at a grocery store could be tracked using a membership or discount card, and those purchases uploaded to a patient workflow management system, providing direct data about the kinds and volumes of food available at the household level, if not at the individual level. Meal choices made at school could be similarly captured using lunch cards or other payment or tracking systems at the school. If menus were also provided to the system, it would allow health service providers to give very granular feedback on how different choices among readily available options might impact an individual's health and/or wellness.

In addition to the benefits in terms of coordinating care and sharing information, embodiments of this disclosure may present technical advantages over conventional systems. As an example, embodiments including an ontology mapper permit system access that would otherwise be impossible or complicated by different data formats and/or different ontologies used within the data. As another example, embodiments which select or cull workflows, either by presenting only workflows assigned to a current system user or as otherwise described, may reduce the processing capacity and/or communications bandwidth needed to process workflow generation, by reducing the number of workflows communicated to and/or presented to any particular user without risk of removing relevant workflows or requiring sequential transmissions and/or processing. In any individual transaction, these reductions may be small in the absolute, however, in systems which cover a large hospital or patient care network, and particularly in HIE-participating systems that may share information across a plurality of networked systems, the cumulative savings in processing capacity and/or communications bandwidth may be significant.

Figure 2:
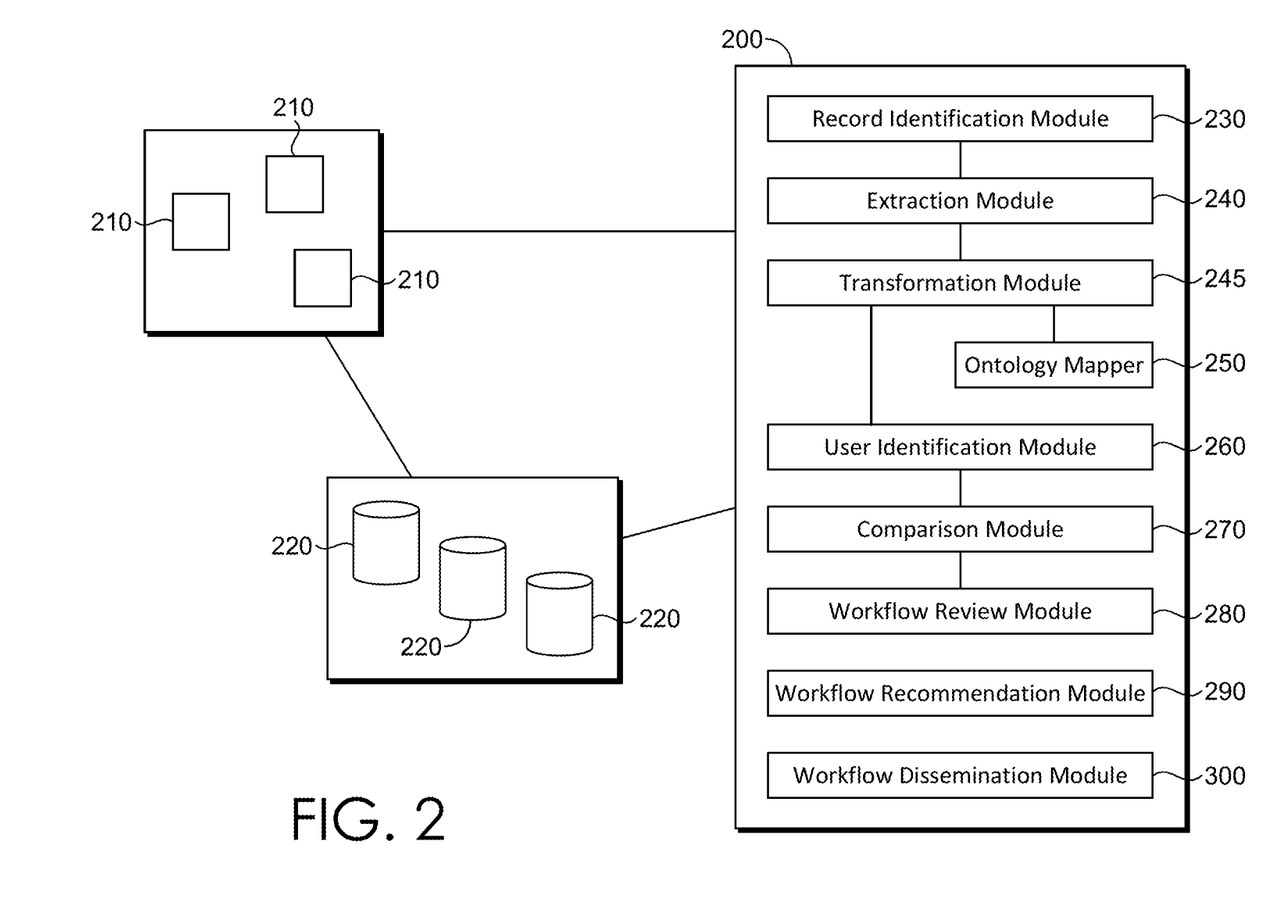
FIG. 2 is a schematic diagram of an exemplary patient care workflow customization system.

An exemplary patient care workflow customization system 200 according to this disclosure is shown in FIG. 2. The system includes one or more patient encounter documentation system 210, such as one or more HIEs, one or more HITs, and/or one or more general purpose (e.g., not specifically designed for healthcare services). Integral to or accessible by the one or more patient encounter documentation system 210 is a database or databases 220 (also shown in FIG. 3). Database or databases 220 store information including, but not limited to, patient health service records, a medical knowledge model and/or database of candidate workflows.

Patient care workflow customization system 200 may include record identification module 230. Record identification module 230 may be configured to search database or databases 220 for health service records related to a particular patient. Records relevant to a particular patient might be identified using one or more data points, including, without limitation, patient name, patient date of birth, patient address, key patient record items (e.g., chronic diagnoses), patient identification numbers (e.g., social security number, insured ID number, or alternate number assigned by a system or provider), and the like. User confirmation may be sought to confirm that the same patient is referenced in records with a moderate likelihood of a match, e.g., where many pieces of information match, but some important items appear to be different, or where key pieces of information match, but several details appear to be different.

Patient care workflow customization system 200 may include extraction module 240. Extraction module 240 may be configured to extract standard health-related data from the health service records identified by record identification module 230. Extraction module 240 may look for diagnostic codes, keywords, images, and the like in the health service records. If the health service records are in a standard format, the native format may be retained.

If the health service records are in different format, transformation module 245 may include or consult an ontology mapper 250 to help correlate related information that has been recorded using different descriptors. Transformation module 245 may transform the extracted data to a standard format, and may store the transformed data. Transformed data may be stored temporarily, such as for a single user session, or longer-term, as for weeks, months, years, or permanently (e.g., unless such file is purposefully deleted). In some embodiments, the transformed data is stored permanently as a longitudinal record for the patient that remains quickly accessible to patient care workflow customization system 200, because the data does not have to be identified and extracted every time a workflow is generated for the particular patient.

Patient care workflow customization system 200 may include a user identification module 260. User identification module 260 may be configured to identify a current system user and the user's role on a patient's care team. User identification module 260 may be a system which controls access to patient care workflow customization system, such as a log-on program or alternate system for establishing user credentials and authorization to access the system (e.g., by a sign-on procedure, use of a physical token, use of an access code or personal identification number, use of biometrics, etc.). If user identification module 260 controls access, a user profile associated with the access credentials may identify the user's role. User identification module 260 may be separate from the system used to control access to patient care workflow customization system 200, or to access related or integrated software, such as a HIT, EMR, patient encounter documentation system, etc. For example, a user may be asked to self-identify the user's role on a particular patient's care team.

Patient care workflow customization system 200 may include a comparison module 270. Comparison module may be configured to compare standardized health information from the health service records accessed for a patient to recommended health service workflows. The recommended health service workflows may be situational, meaning that they are reflective of a patient's symptoms and/or conditions, possibly including the patient's gender and age. For example, the situationally recommended health service workflows for a 5-year-old patient may include CDC-recommended vaccines for 5-year-olds. The recommended health service workflows may be identified by comparison to a database of health service workflows and/or by comparison to a medical knowledge model. A medical knowledge model may provide more sophisticated tailoring to an individual, and, in that aspect, may be preferred to a database. However, use of a medical knowledge model to generate an initial set of recommended workflows may be more time- and or system-resource intensive, and, in that aspect, a simpler database may be preferred.

Patient care workflow customization system 200 may include a workflow review module 280. Workflow review module 280 may check the initially recommended health service workflows against the current user's role on the patient's health care team, identifying those workflows which are actionable by the user. A workflow may be actionable by a user if the role has no known limitations that would prohibit the user from performing the requested task. A workflow may be actionable by a user if the user role and/or the workflow have been identified as compatible, i.e., if the user role has been associated with individual workflows or groups or types of workflows that the user can act on, or, instead of or in addition to the user role definition, the workflow has been associated with user roles that can carry out the workflow. A workflow may be identified as actionable by a user if the user or users in the same or similar roles have completed the same or similar workflows in the past, either in the current venue or in other, related venues.

Patient care workflow customization system 200 may include a workflow reconciliation module 290. Workflow reconciliation module 290 may be configured to eliminate actionable health service workflows which are duplicative, which appear from the information derived from the health service records to be in-process (e.g., if the workflow has been initiated by another provider on the patient's care team), which appear from the information derived from the health service records to be complete and up-to-date, or which are untimely (e.g., a workflow which requires attention, but not in the context of the current visit or encounter).

Patient care workflow customization system 200 may include a workflow dissemination module 300. Workflow dissemination module 300 may transfer recommended health service workflows from the current user to a different user on the patient's care team. For example, workflow dissemination module 300 may automatically transfer a recommended health service workflow to one or more other users if the workflow is not actionable by the current user. The transfer may be made to one or more other users for whom the workflow would be actionable. Workflow dissemination module 300 may reassign a workflow to another user or users if the current user closes the patient record, logs out of the system, or otherwise indicates the current user has completed a particular patient encounter, and one or more workflows assigned to the current user (now the previous user) is incomplete. Workflow dissemination module 300 may also provide a user the ability to send a workflow to a different user. This may be useful, for example, for delegation of tasks and/or escalation of tasks, e.g., if a provider believes that a particular task or assessment is better completed by a different user role and or a particular provider. Workflow dissemination module 300 may allow a user to complete a workflow and indicate that the workflow should be assigned to a different user or different user role in the future.

Figure 3:
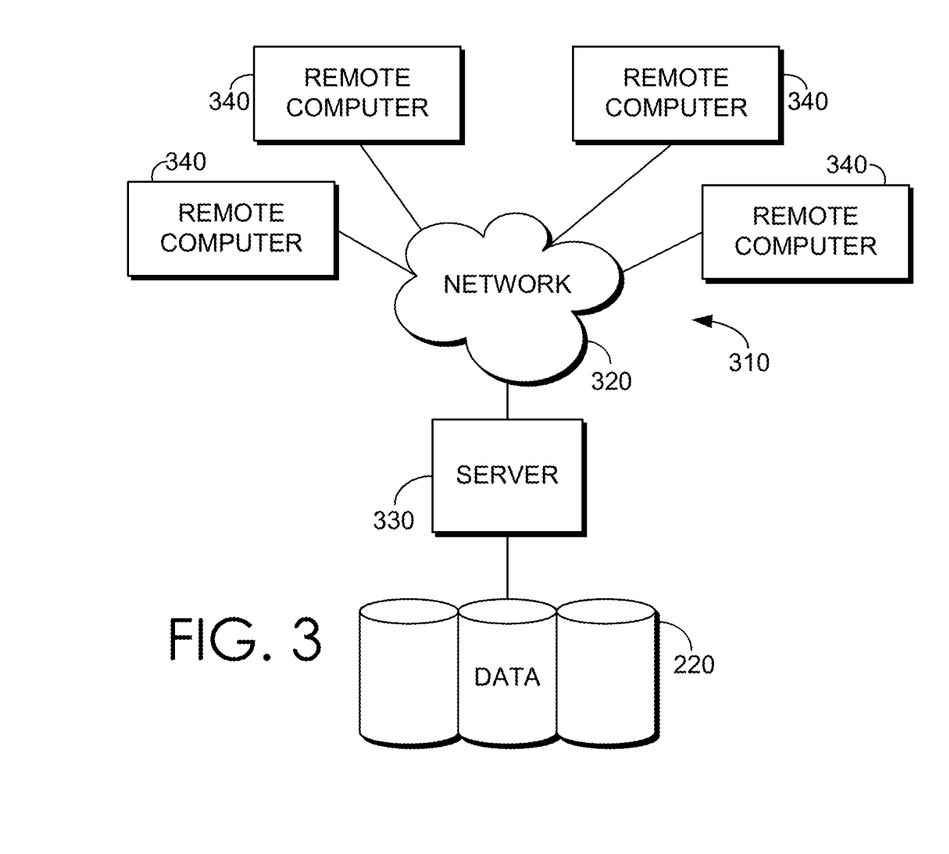
FIG. 3 is a schematic view of an exemplary computing system useful for implementing embodiments of the disclosure.

Patient care workflow customization system 200 may be operated in an exemplary computing environment 310 as shown in FIG. 3. Exemplary computing environment 310 includes at least one general purpose computing device in the form of a control sever 330. Components of control server 330 may include, without limitation a processing unit, internal system memory, and a suitable system bus for coupling various system components, including database cluster 220, with the control server 330. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus.

The control server 330 typically includes therein, or has access to, a variety of computer-readable media, for instance, database cluster 220. Computer-readable media can be any available media that may be accessed by control server 330, and includes volatile and nonvolatile media, as well as removable and non-removable media. By way of example, and not limitation, computer-readable media may include computer-storage media and communication media. Computer-storage media may include, without limitation, volatile and nonvolatile media, as well as removable and non-removable media implemented in any method or technology for storage of information, such as computer readable instructions, data structures, program modules, or other data. In this regard, computer-storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 22. Computer-storage media may exclude signals per se. Computer-readable media may exclude signals per se.

Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media. The computer-storage media discussed above and illustrated in FIG. 3, including database cluster 220, provide storage of computer readable instructions, data structures, program modules, and other data for the control server 330.

The control server 330 may operate in a computer network 320 using logical connections to one or more remote computers 340. Remote computers 340 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices and the clinician's home or the patient's own home or over the Internet. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 340 may also be physically located in non-traditional medical care environments so that the entire health care community may be capable of integration on the network. The remote computers 340 may be personal computers, servers, routers, network PCs, peer devices, other common network nodes, or the like, and may include some or all of the elements described above in relation to the control server 330. The devices can be personal digital assistants or other like devices.

Exemplary computer networks 3200 may include, without limitation, local area networks (LANs) and/or wide area networks (WANs). Such networking environments are commonplace in offices, enterprise-wide computer networks, intranets, and the Internet. When utilized in a WAN networking environment, the control server 330 may include a modem or other means for establishing communications over the WAN, such as the Internet. In a networked environment, program modules or portions thereof may be stored and/or executed on the control server 330, in the database cluster 220, or on any of the remote computers 340. For example, and not by way of limitation, various application programs and/or data may reside on the memory associated with any one or more of the remote computers 340. It will be appreciated by those of ordinary skill in the art that the network connections shown are exemplary and other means of establishing a communications link between the computers (e.g., control server 330 and remote computers 340) may be utilized.

In operation, a user may enter commands and information into the control server 330 or convey the commands and information to the control server 330 via one or more of the remote computers 340 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 330. In addition to a monitor, the control server 330 and/or remote computers 340 may include other peripheral output devices, such as speakers and a printer.

Many other internal components of the control server 330 and the remote computers 340 are not shown because such components and their interconnection are well known. Accordingly, additional details concerning the internal construction of the control server 330 and the remote computers 340 are not further disclosed herein.

Methods and systems of embodiments of the present invention may be implemented in a WINDOWS or LINUX operating system, operating in conjunction with an Internet-based delivery system. One of ordinary skill in the art will recognize that the described methods and systems can be implemented in any alternate operating system suitable for supporting the disclosed processing and communications. As contemplated, the methods and systems of embodiments of the present invention may also be implemented on a stand-alone desktop, personal computer, cellular phone, smart phone, PDA, or any other computing device used in a healthcare environment or any of a number of other locations. Nonetheless, when networked and/or programmed as described herein, the system does more than the individual, generic devices could do.

In some aspects, computer storage media may contain computer executable instructions thereon. The instructions, when executed by a computer, may cause the computer to identify health service records for a patient. The instructions may cause the computer to extract information from the health service records for the patient. The instructions may cause the computer to transform the information extracted from the health service records into standardized information. The instructions may further cause the computer to compare standardized information from the health service records to situationally recommend health service workflows associated with a patient's symptoms and/or conditions and generate recommended health service workflows for the patient.

The instructions may cause the computer to identify the health service role of a user of a patient care documentation system. The instructions may cause the computer to determine which, if any, of the recommended health service workflows are actionable by the user. The instructions may cause the computer to eliminate or modify actionable health service workflows which are duplicative, appear from the standardized information to be in process, appear from the standardized information to be complete and up-to-date, or are untimely, to yield a set of remaining health service workflows. The instructions may cause the computer to present the set of remaining health service workflows to the user.

From the foregoing, it will be seen that this disclosure is well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

What is claimed is:

1. A method for customizing a patient care workflow, the method comprising: identifying two or more health service records for a patient, the two or more health service records generated by different venues and being stored in different data structures; extracting information from the two or more health service records; converting the information extracted from the two or more health service records into standardized information, the standardized information having a standardized data structure; comparing the standardized information from the health service records to situationally recommended health service workflows associated with a patient's symptoms and/or conditions; based on the comparing generating recommended health service workflows for the patient; automatically identifying the health service role of a user of a patient care documentation system, the health service role being associated with a set of permissions and authorizations; based at least in part on the set of permissions and authorizations, automatically determining which, if any, of the recommended health service workflows are actionable by the user; based on the determining, automatically eliminating non-actionable health service workflows of the recommended health service workflows and actionable health service workflows of the recommended health service workflows which are duplicative, appear from the standardized information to be in process, appear from the standardized information to be complete and up-to-date, or require attention but not in a current visit or encounter to yield a set of remaining health service workflows; and presenting, in a user interface, the set of remaining health service workflows to the user and any treatment scheduled between the patient and another provider that is actionable by the user.

2. The method of claim 1, wherein the two or more health service records are related to the same or similar conditions or symptoms.

3. The method of claim 1, wherein the two or more health service records are related to different conditions or symptoms.

4. The method of claim 1, further comprising extracting information in a format from the two or more health service records and transforming the format of the information to produce the standardized information.

5. The method of claim 1, wherein at least one of two or more different health service venues does not provide health care services.

6. The method of claim 1, wherein the two or more health service records comprise one or more of insurance claim records, clinical records, wellness records, satisfaction records, payer records, and pharmacy records.

7. The method of claim 1, further comprising comparing the standardized information to a medical knowledge model to infer possible conditions or symptoms for the patient.

8. The method of claim 1, wherein the set of remaining health service workflows comprises one or more of recommended orders for the user to place, recommended tasks for the user to complete, recommended condition review, recommended assessment, educational or reference material for the user or the patient, and combinations thereof.

9. The method of claim 1, further comprising transferring recommended health service workflows which are not actionable by the user to one or more additional users for whom the recommended health service workflows would be actionable.

10. The method of claim 1, wherein the set of remaining health service workflows are customized for the user based on a health service venue in which the user is addressing the patient.

11. The method of claim 1, wherein the set of remaining health service workflows are customized for the user based on user-indicated preferences.

12. A system for customizing a patient care workflow, the system comprising: a processor; and a computer storage medium storing computer-usable instructions that, when used by the processor, cause the processor to: identify two or more health service records for a patient, the two or more health service records being from different venues and being stored in different data structures; extract information from the two or more health service records; convert the information extracted from the two or more health service records into standardized information, the standardized information having a standardized data structure; compare the standardized information from the health service records to situationally recommended health service workflows associated with a patient's symptoms and/or conditions; based on the comparison, generate recommended health service workflows for the patient; automatically identify a health service role of a user of a patient care documentation system, the health service role being associated with a set of permissions and authorizations; based at least in part on the set of permissions and authorizations, automatically determine which, if any, of the recommended health service workflows are actionable by the user; based on the determining, automatically eliminate non-actionable health service workflows of the recommended health service workflows and actionable health service workflows of the recommended health service workflows which are duplicative, appear from the standardized information to be in process, appear from the standardized information to be complete and up-to-date, or require attention but not in a current visit or encounter to yield a set of remaining health service workflows;

and present, in a user interface, the set of remaining health service workflows to the user and any treatment scheduled between the patient and another provider that is actionable by the user.

13. The system of claim 12, further comprising extracting information from the health service records for the patient.

14. The system of claim 13, further comprising transforming the information extracted from the health service records into the standardized information.

15. The system of claim 12, further comprising sending recommended health service workflows which are not actionable by the user to one or more other health service providers associated with the patient for whom the recommended health service workflows would be actionable.

16. Computer storage media, excluding signals per se, containing computer executable instructions which, when executed by a computer, cause the computer to: identify two or more health service records for a patient, the two or more health service records from different venues and being stored in different data structures; extract information from the two or more health service records; convert the information extracted from the two or more health service records into standardized information, the standardized information having a standardized data structure; compare the standardized information from the health service records to situationally recommended health service workflows associated with a patient's symptoms and/or conditions; based on the comparison generate recommended health service workflows for the patient; automatically identify a health service role of a user of a patient care documentation system, the health service role being associated with a set of permissions and authorizations; based at least in part on the set of permissions and authorizations, automatically determine which, if any, of the recommended health service workflows are actionable by the user and actionable health service workflows of the recommended health service workflows which are duplicative, appear from the standardized information to be in process, appear from the standardized information to be complete and up-to-date, or require attention but not in a current visit or encounter to yield a set of remaining health service workflows; based on the determining, automatically eliminating non-actionable health service workflows of the recommended health service workflows; and present, in a user interface, the set of remaining health service workflows to the user and any treatment scheduled between the patient and another provider that is actionable by the user.

17. The computer storage media of claim 16, wherein the instructions further cause the computer to extract information from the health service records for the patient.

18. The computer storage media of claim 17, wherein the instructions further cause the computer to transform the information extracted from the health service records into the standardized information.

\* \* \* \* \*